United States Patent [19]

Nozaki

[11] Patent Number: 4,687,876
[45] Date of Patent: Aug. 18, 1987

[54] PRODUCTION OF 1,7-OCTADIENE FROM BUTADIENE

[75] Inventor: Kenzie Nozaki, Houston, Tex.

[73] Assignee: Shell Oil Company, Houston, Tex.

[21] Appl. No.: 589,407

[22] Filed: Mar. 16, 1984

Related U.S. Application Data

[63] Continuation of Ser. No. 144,806, Apr. 29, 1980, abandoned, which is a continuation-in-part of Ser. No. 16,211, Mar. 5, 1979, abandoned, which is a continuation-in-part of Ser. No. 890,116, Mar. 27, 1978, abandoned.

[51] Int. Cl.$^4$ .................................................. C07C 2/18
[52] U.S. Cl. ...................................... 585/509; 585/511
[58] Field of Search ................................ 585/509, 511

[56] References Cited

U.S. PATENT DOCUMENTS

| 3,732,328 | 5/1973 | Wright | 260/680 B |
|---|---|---|---|
| 3,823,199 | 7/1974 | Wright | 260/680 B |
| 3,970,592 | 7/1976 | Ploner | 260/680 B |
| 4,180,694 | 12/1979 | Nozaki | 585/511 |
| 4,196,135 | 4/1980 | Enomoto et al. | 585/509 |
| 4,229,606 | 10/1980 | Nozaki | 585/509 |
| 4,243,829 | 1/1981 | Pittman et al. | 585/514 |

FOREIGN PATENT DOCUMENTS 1341324 12/1973 United Kingdom ............ 260/680 B

OTHER PUBLICATIONS

Gardner et al, Tetrahedron Letters, No. 2, pp. 163–164, (1972).
Raffia et al, J. Organometallic Chemistry, 55, pp. 405–407, (1973).

Primary Examiner—J. E. Evans
Assistant Examiner—Joseph A. Boska

[57] ABSTRACT

In the process for preparing 1,7-octadiene by hydrodimerizing butadiene in the presence of a solubilized palladium or palladium compound, a tertiary phosphine, formic acid, a base and optionally a solvent, improved rates of conversions of butadiene to 1,7-octadiene are obtained by carrying out the process in the presence of supported palladium, platinum or rhodium.

6 Claims, No Drawings

PRODUCTION OF 1,7-OCTADIENE FROM BUTADIENE

This is a continuation of application Ser. No. 144,806, filed Apr. 29, 1980, now abandoned which in turn is a continuation-in-part of copending application Ser. No. 16,211 filed Mar. 5, 1979 now abandoned which, in turn, is a continuation-in-part of application Ser. No. 890,116, filed Mar. 27, 1978, now abandoned.

BACKGROUND OF THE INVENTION

1. Field of the Invention

The present invention relates to the production of 1,7-octadiene by hydrodimerizing butadiene.

2. Description of the Prior Art

Linear dimerization of butadiene provides a source of $C_8$ unsaturated hydrocarbon intermediates useful for the synthesis of diacids, diesters, diols or diamines. A particularly preferred dimer is 1,7-octadiene which has terminal double bonds and allows the production of product having only terminal functional groups.

Wright in U.S. Pat. No. 3,732,328, issued May 8, 1973, prepares mixtures of octadienes by reacting butadiene in the presence of a palladium compound, a polar solvent, a reducing agent and a tertiary phosphine.

Wright in U.S. Pat. No. 3,823,199, issued July 9, 1974, prepares mixtures of octadienes by reacting butadienes in the presence of palladium metal or a palladium compound, a non-polar solvent, a reducing agent and a tertiary phosphine.

Wright in British Pat. No. 1,341,324 issued Dec. 9, 1973 discloses processes similar to above but uses amine solvents.

Gardner et al, Tetrahedron Letters No. 2, pp. 163-164 discloses the production of mixtures of octadienes by reacting butadiene in the presence of palladium salts, an organic base, formic acid and a phosphine.

Roffia et al, Journal of Organometallic Chemistry, 55 (1973) 405-407 utilizes a triphenyl phosphine-zero valent palladium complex catalyst in benzene in the presence of formic acid to dimerize butadiene. Although Roffia et al reported a 75% butadiene conversion, only 22% of the product was 1,7-octadiene.

None of the references cited above have disclosed the concept of increasing the rate of formation of 1,7-octadiene by also using a supported palladium, platinum and/or rhodium catalyst in conjunction with solubilized palladium catalyst. Increased rates are important to commercial ventures. High selectivities and conversions at low rates can make a venture unprofitable. The instant invention provides significantly enhanced rates over those of the prior art.

SUMMARY OF THE INVENTION

The process of this invention is directed to the hydrodimerization of butadiene to 1,7-octadiene at high rates by reacting the butadiene in the presence of solubilized palladium or a solubilized palladium compound, formic acid, a base, optionally a solvent, a tertiary phosphine and a supported palladium, platinum or rhodium catalyst. The addition of the supported catalyst to the solubilized palladium tertiary phosphine complex conventionally utilized provides for a significant increase in the rate of conversion of butadiene to 1,7-octadiene as compared to rates utilizing solubilized palladium alone or supported palladium alone.

DESCRIPTION OF THE PREFERRED EMBODIMENTS

Solvents are not essential to the process of this invention, but a good organic solvent can promote the rate of reaction by a factor of two or more.

Wright in above-cited U.S. Pat. No. 3,823,199 cites the use of non-polar solvents such as paraffinic, cycloparaffinic or aromatic which are useful in the process of this invention. The solvent can be a paraffin or cycloparaffin containing 5 to 16 carbon atoms, such as hexane, dodecane, pentadecane, cyclohexane, methylcyclohexane and the like. Suitable solvents also include aromatic hydrocarbons such as benzene, lower alkyl substituted aromatic hydrocarbons such as toluene, m-, p- and o-xylene, halogenated aromatic hydrocarbons including chloro, bromo and iodo substituted, such as chlorobenzene and the like. Halogenated lower aliphatic compounds such as chloroform, methylene chloride, carbon tetrachloride and the like may be used, in particular chloroform is preferred.

Further useful are the amine solvents cited by Wright in above-noted British Pat. No. 1,341,324. A wide range of amines are useful provided that they are liquid under reaction conditions. Tertiary amines are preferred to primary and secondary amines. Suitable amine solvents include alkylamines, cycloalkylamines, arylamines and heterocyclic amines such as morpholine, pyridine, piperazine and piperidine. Examples of these classes of amines are the lower alkylamines containing 2 to 6 carbon atoms in each alkyl group such as triethylamine; monocyclohexylamine, and N-alkyl-cyclo-hexylamines containing up to 12 carbon atoms; aniline and N-alkylanilines containing up to 12 carbon atoms and N-alkylmorpholines containing up to 12 carbon atoms.

Preferred solvents are those of moderate coordinating ability, and which include nitriles such as lower alkyl nitriles, hydrocarbon aromatic nitriles including acetonitrile, benzonitrile and the like, amides including benzamide, acetamide, mono- and di-substituted amides where the substituent is preferably lower alkyl. Suitable substituted amides include N-methyl acetamide, N,N dimethyl acetamide and dimethylformamide. Dialkyl sulfoxides such as dimethyl sulfoxide and sulfones such as sulfolane and alkyl-substituted sulfolane are satisfactory. Simple ethers such as the dilower alkyl ethers including dimethyl ether, diethylether, and the like function satisfactorily. Hydrocarbon aromatic ethers such as the lower alkyl phenyl ethers may also be used, and include methyl phenyl ether (anisole), ethyl phenyl ether (phenetole) and the like. Cyclic, saturated hydrocarbon ethers such as tetrahydrofuran, tetrahydropyran and the like are also suitable solvents. Lower alkyl diethers such as dimethoxy ethane, and the like may be used. In addition, the cyclic diethers such as 1,4-dioxane are also suitable solvents.

Simple lower alkyl esters of lower alkanoic acids such as ethyl acetate, methyl acetate, methyl butyrate and the like as well as cyclic diesters such as ethylene carbonate are also suitable solvents of moderate coordinating ability. Ketones, including lower aliphatic ketones such as methyl ethyl ketone and hydrocarbon aromatic ketones such as acetophenone are also satisfactory solvents. Lower mono- and di-alkanols such as isopropanol, ethylene glycol and the like may be used if desired. The preferred solvents of moderate coordinating ability include nitriles, formamides, such as dimethylformamide, dilower alkyl ethers, lower alkyl phenyl ethers, simple lower alkyl esters of lower alkanoic acids, ketones and lower alkanols.

The particularly preferred solvents utilized in this invention include benzene, dimethylformamide, chlorobenzene, anisole, N,N-dimethylacetamide, nitromethane, ethyl acetate, isopropanol, benzonitrile, chloroform, methyl ethyl ketone, acetonitrile, diethylether, acetophenone, toluene, ethylene glycol, ethylene carbonate, propylene carbonate and sulfolane. Particularly desired solvents are nitromethane, ethylene carbonate and propylene carbonate.

The preferred organic solvents will have carbon numbers ranging from 1 to about 20. Particularly desired solvents are those which give two-phase systems which allow easy product separation such as, for example, nitromethane, ·ethylene carbonate and propylene carbonate.

The amount of solvent added should be sufficient to dissolve the palladium compound-tertiary phosphine complex.

The formic acid is utilized as a source of hydrogen for the process. It is present in the reaction mixture as a salt of the base promoter utilized. It is thought that dissociation of the formic acid-base salt provides a suitable amount of formic acid necessary to provide the required hydrogen. Excess free acid present in the reaction mixture has an inhibitory effect on the reaction.

It is desirable that some formic acid, as the salt, be present during the entire course of the reaction. When operating the process batch-wise, this can be accomplished by adding a stoichiometric amount of formic acid initially, 1 mole of formic acid for every 2 moles of butadiene, or by continuously or periodically adding additional amounts of formic acid. It is essential, however, that the ratio of base to formic acid present in the reaction medium never be less than 1.

The base must be one which can neutralize formic acid according to the reaction:

$$HCOOH + B \rightarrow HCOO^- HB^+.$$

The base may be either insoluble or soluble in the reaction medium.

The base may be organic or inorganic. Suitable organic bases typically have dissociation constants greater than $10^{-8}$ and include tertiary amine such as triethylamine, tributyl amine, dimethylethyl amine, lutidine, tripropyl amine, N-methyl morpholine, isoquinoline. N-methyl-2,2,6,6-tetramethyl piperidine, 2,8-(dimethylamine)naphthalene and the like.

Suitable inorganic bases include ammonia, the hydroxide bases such as sodium hydroxide, potassium hydroxide, calcium hydroxide; ammonium hydroxide; the carbonates and bicarbonates such as sodium carbonate, sodium bicarbonate, potassium carbonate, potassium bicarbonate, calcium carbonate and the like; the weak bases such as sodium acetate, potassium acetate, ammonium carbonate, ammonium acetate and the like. When the inorganic bases are utilized, small amounts of water may be present.

The mole ratio of base to formic acid must be at least equal to 1. When organic bases are utilized, excess base may be utilized as a solvent or the amine-base salt may be used as the solvent.

The conventional catalyst used in the process of this invention is palladium or a palladium compound complexed with a tertiary phosphine ligand. The palladium may be in any of its possible valence states, e.g. 0, +2, etc. Suitable palladium compounds include the palladium carboxylates, particularly palladium carboxylates derived from alkanoic acids containing up to six carbon atoms such as palladium acetate, complexes such as palladium acetylacetonate, bisbenzonitrile palladium (II) and lithium palladous chloride as well as the palladium halides, nitrates and sulfates such as palladous chloride and palladium nitrate (Pd(NO$_3$)$_2$(OH)$_2$) and palladium sulfate. Suitable palladium-phosphine complexes are Pd(R$_3$P)$_2$ and Pd(R$_3$P)$_3$. The solubilized palladium is present in the reaction mixture in catalytic amounts; preferably from about $10^{-1}$ to $10^{-6}$ and most preferably from about $10^{-2}$ to about $10^{-5}$ molar.

Any tertiary phosphine which can be dissolved in the reaction solvent may be used. The bisphosphines, such as 1,3-bisphenylphosphinopropane and 1,4-bisdiphenylphosphineobutane, will not function in the present invention as the tertiary phosphine, the butadiene conversions obtained are unsatisfactory. Accordingly, it is preferred to use a mono-phosphine. Suitable phosphines are represented by the formula:

$$R_a - P - R_b$$
$$|$$
$$R_c$$

wherein R$_a$, R$_b$ and R$_c$ may be the same or different and are selected from aryl such as phenyl, p-tolyl, o-tolyl, m-tolyl, p-chlorophenyl, phenoxy, p-methylphenoxy, p-anisoly, m-anisoyl and the like, alkyl of 1 to 8 carbon atoms, preferably 1 to 5 carbon atoms, alkoxy having from 1 to 8 carbon atoms, but preferably from 1 to 3 carbon atoms. Preferably, R$_a$, R$_b$ and R$_c$ represent aryl, alkyl, or a mixture thereof. The more preferred tertiary phosphines, are the triaryl and trialkyl phosphines. The most preferred tertiary phosphines have the general formula:

$$R_1R_2R_3P$$

wherein R$_1$ is benzyl or branched alkyl, aralkyl, alkenyl, and cycloalkyl having from 3 to about 10 carbon atoms with branching occuring at a carbon atom no more than two carbon atoms from the phosphorus atom and R$_2$ and R$_3$ are R$_1$ or independently are alkyl, alkenyl or aryl having from 1 to about 10 carbon atoms.

Illustrative of the R$_1$ moiety are, for alkyl, isopropyl, sec-butyl, tert-butyl, isobutyl, neopentyl, sec-pentyl, tert-pentyl, 2-methylbutyl, sec-hexyl, tert-hexyl, 2,2-dimethylpropyl; for aryalkyl, alpha-methylbenzyl, alpha, alpha-dimethylbenzyl, alpha-methyl-alpha-ethylbenzyl, phenylethyl, phenylisopropyl, phenyl-tert-butyl; for alkenyl, allyl, crotyl, methallyl, 1-methylethenyl, 1-methyl-2-propenyl, 1,1-dimethyl-2-propenyl, 1-methyl-3-butenyl; and, for cycloalkyl, cyclopropyl, cyclobutyl, cyclo-pentyl, cyclohexyl, cycloheptly cycloalkyl and the like.

Illustrative of the R$_2$ and R$_3$ are, for example, methyl, ethyl, propyl, butyl, pentyl, hexyl, octyl, nonyl and decyl for alkyl; allyl, crotyl and methallyl for alkenyl, and phenyl, tolyl, xylyl, ethylphenyl, propylphenyl for aryl. Two or more of the instant phosphines may be used in the same reaction or another phosphine may be replaced by reacting in situ one of the instant phosphines. The mole ratio of tertiary phosphine to palladium is at least 1. Preferably the mole ratio of phosphine to palladium ranges from about 1:1 to about 1:20 and preferably from about 2:1 to about 5:1. The use of the phosphines of the invention provides extremely high selectivities to 1,7-octadiene.

The promotive supported co-catalyst of the invention comprises a metal selected from the group consisting of palladium, platinum, rhodium or mixtures thereof supported on an inert support. The support employed in these co-catalysts in its broadest aspects is selected from the large number of conventional, porous catalyst carriers or supports materials which are essentially inert under reaction conditions. Such conventional materials may be of natural or synthetic origin. Very suitable supports comprise those of siliceous, aluminous, and carbonaceous compositions. Specific examples of suitable supports are the alumina oxides (including the materials sold under the trade name "alundum"), charcoal, activated carbon, pumice, magnesia, zirconia, kieselguhr, fuller's earth, silicon carbide, calcium carbonate, porous agglomerates comprising silicon and/or silicon carbide, silica, mullite, selected days, artificial and natural zeolites and ceramics. Preferred supports are the aluminas, the silicas, and the carbons such as activated charcoal and graphite.

The co-catalysts are prepared in a conventional manner by impregnating the support with a solution of a suitable metal compound, and then heating the impregnated support in a reducing environment to reduce the metal compound to the metal.

Suitable impregnating solutions are made, for example, from metal carboxylates such as acetates, halides, nitrates, sulfates and the like. Typical examples are aqueous solutions of palladous chloride, palladous nitrate, palladous acetate, platinium chloride chloroplatininc acid, rhodium nitrate and the like.

The co-catalysts utilized in the invention are not novel per se and find use today in many industries, especially the petrochemical industries, for the hydrogenation and dehydrogenation of organic compounds. The supported metal catalysts are readily available commercially.

Catalysts according to this invention preferably contain from about 0.0001 to about 30, more preferably from about 0.001 to about 10 and most preferably from about 0.001 to about 1 percent by weight of metal based on the total weight of the catalyst. The use of larger amounts of catalytic metal is not excluded but is generally uneconomic due to the high price of the metals.

The ratio of the metal in the supported catalyst to the solubilized palladium ranges from about 0.001 to about 10 preferably from about 0.001 to about 3, and more preferably from about 0.001 to about 1.

The supported co-catalyst may be used in bulk or powdered form. The powdered form (less than about 100 mesh) is useful in a batch reaction utilizing a homogeneous conventional palladium-phosphine complex catalyst. In continuous processes the co-catalyst may be used as pellets, rings or the like in a fixed bed in conjunction with a homogeneous conventional palladium-phosphine complex catalyst or may be admixed in a fixed bed with a heterogeneous palladium phosphinated resin complex.

The addition of carbon dioxide to the reaction system has been found to increase the extent of butadiene conversion, but does not affect the selectivity. When it is desired to use carbon dioxide to increase the conversion rate, the partial pressure of the $CO_2$ in the reaction system may be from about 10 to about 100 psia. Since carbon dioxide is a by-product of the process, it is possible to generate sufficient carbon dioxide in situ to enhance the conversion rates.

The process can be either continuous or batch. The reaction temperature of the process is not critical, however, it is preferred to maintain the reaction between about 0° to about 100° C. preferably between about 20° to about 70° C. The process is conducted under a sufficient pressure to maintain liquid phase conditions at the reaction temperature. Typically the pressure is autogeneous.

The process of this invention is particularly useful when applied to a BBB stream from an oil pyrolysis unit. These BBB streams are the $C_4$ cut from a thermal cracking unit typically containing 30–40% butadiene, 20–35% isobutene and 20–30% n-butenes and many minor components including about ½% of vinylacetylene. Vinyl acetylene is a moderate retarder for butadiene hydrodimerization. The addition of from about 0.2 to about 4 percent by volume of hydrogen along with the supported metal co-catalyst of this invention of the BBB hydrodimerization system eliminates the retardation, presumably by hydrogenating the vinylacetylene.

The invention is thus a process for preparing 1,7-octadiene by hydrodimerizing 1,3-butadiene which comprises contacting the 1,3-butadiene with (a) a solubilized palladium catalyst, (b) a supported metal co-catalyst selected from the group consisting of palladium, platinum, rhodium and mixtures thereof wherein the metal is present on the carrier in amounts ranging from about 0.001 to about 30, preferably 0.001 to about 10 percent by weight of the total supported catalyst and the ratio of the metal in the supported catalyst to the solubilized palladium ranges from about 0.001 to about 10, preferably from about 0.001 to about 3 and more preferaby from about 0.001 to about 1, (c) a tertiary phosphine (d) a base and (e) optionally a solvent. The temperature of the process ranges from about 0° C. to about 100° C., the solubilized palladium ranges from about $10^{-1}$ to about $10^{-6}$ molar, the mole ratio of tertiary phosphine to solubilized palladium is at least 1 and the molar ratio of base to formic acid is at least 1. The carrier is preferaby siliceous, aluminous or carbonaceous.

The process of this invention will be further described by the following illustrative embodiments which are provided for illustration and are not to be construed as limiting the invention.

ILLUSTRATIVE EMBODIMENTS

Illustrative Embodiment I

To an 80 milliliter glass-lined autoclave were charged $2.7 \times 10^{-5}$ moles of palladium as a 10% water solution of $Pd(NO_3)_2(OH)_2$, $5.4 \times 10^{-5}$ moles (isopropyl)$_3$ phosphine, 2.5 grams of triethylamine formic acid salt, 10 milliliters of pyridine and 2 grams of 1,3-butadiene. The stirred reactor was heated to 45° C. for 1 hour, cooled and the product was analyzed by gas chromatography for the amount of 1,7-octadiene present. This case provided the base case for solubilized palladium alone and is shown in Table I as example I. In this base case, the soluble palladium catalyst is present at a concentration of about $1.8 \times 10^{-3}$ molar.

The above experiment was repeated four additional times using 0.0001 g, 0.001 g, 0.01 g and 0.1 g of 10% w palladium on carbon catalyst (Baker and Co., Inc.) in addition to the solubilized catalyst present at a concentration of $1.8 \times 10^{-3}$ molar. The results are shown in Table I as examples 2–5. Column 4 of the Table gives the average rate (R) of formation of 1,7-octadiene in the product per hour. Column 5 reports the percentage of the butadiene reactant originally present in the reaction which is converted to the desired 1,7-octadiene product in one hour reaction time. In cases where the conversion to 1,7-octadiene was between 5 and 95% in one hour reaction time, the selectivity to 1,7-octadiene was about 98%. Column 6 is the rate (R) normalized to the rate obtained using solubilized palladium alone ($R_o$), and column 7 gives the ratio of supported palladium to solubilized palladium.

TABLE I

| Example | Moles of Palladium Added Solubilized | Moles of Palladium Added Supported | Rate, % w 1,7-Octadiene In Product Per Hour | % of Butadiene Reactant Converted to 1,7-Octadiene In 1 Hour | Normalized Rate R $R_o$ | Supported Pd/Solubilized Pd |
|---|---|---|---|---|---|---|
| 1 | $2.7 \times 10^{-5}$ | None | 5.87 | 34.5 | 1.0 | — |
| 2 | $2.7 \times 10^{-5}$ | $9.4 \times 10^{-8}$ | 8.5 | 50 | 1.4 | 0.0035 |
| 3 | $2.7 \times 10^{-5}$ | $9.4 \times 10^{-7}$ | 16.0 | 94 | 2.7 | 0.035 |
| 4 | $2.7 \times 10^{-5}$ | $9.4 \times 10^{-6}$ | 10.9 | 64 | 1.9 | 0.35 |
| 5 | $2.7 \times 10^{-5}$ | $9.4 \times 10^{-5}$ | 5.84 | 34.2 | 1.0 | 3.5 |
| 6 | None | $9.4 \times 10^{-7}$ | 0.04 | 0.24 | — | — |
| 7 | None | $9.4 \times 10^{-6}$ | 0.33 | 1.9 | — | — |
| 8 | None | $9.4 \times 10^{-5}$ | 2.28 | 13.4 | — | — |

Examples 6–8 are repeats of the above experiments using only supported palladium alone.

To an 80 milliliter glass-lined autoclave were charged $2.7 \times 10^{-5}$ moles of palladium as a 10% water solution of $Pd(NO_3)_2(OH)_2$, $5.4 \times 10^{-5}$ moles (isopropyl)$_3$ phosphine, 2.5 grams of triethylamine formic acid salt, 10 milliliters of pyridine and 2 grams of 1,3-butadiene (concentration of soluble palladium being about $1.8 \times 10^{-3}$ molar) and the appropriate supported metal co-catalyst from Table II. The stirred reactor was heated to 45° C. for 1 hour, cooled and the product was analyzed by gas chromatography for the amount of 1,7-octadiene present. The results are shown in Table II. All powders used were less than 100 mesh.

TABLE II

| Supported Metal Co—Catalyst | Moles of Supported Pd | Rate, % w, 1,7-Octadiene In Product Per Hour | % of Butadiene Reactant Converted to 1,7-Octadiene In 1 Hour |
|---|---|---|---|
| None | — | 5.87 | 34.5 |
| (1)0.05 g of 0.2% Pd/C | $9.4 \times 10^{-7}$ | 10.0 | 58.8 |
| (3)0.01 g of 10% Pd/Al$_2$O$_3$ | $9.4 \times 10^{-7}$ | 14.07 | 83 |
| (4)0.02 g of 5% Pd/Al$_2$O$_3$ | $9.4 \times 10^{-6}$ | 13.25 | 78 |
| (5)0.02 g of 5% Pd/CaCO$_3$ | $9.4 \times 10^{-6}$ | 9.58 | 56.3 |
| (6)0.1 g of 1% Pt/C | $9.4 \times 10^{-6}$ | 7.79 | 45.8 |
| (7)0.02 g of 5% Rh/Al$_2$O$_3$ | $9.4 \times 10^{-6}$ | 9.41 | 55.4 |
| (8)0.02 g of 5% Ru/C | $9.4 \times 10^{-6}$ | 5.0 | 29.5 |
| (9)0.1 g of 10% Ni/C | $9.4 \times 10^{-5}$ | 5.35 | 31.5 |
| (9)0.01 g of 10% Co/C | $9.4 \times 10^{-6}$ | 5.59 | 33 |
| (9)0.01 g of 10% Fe/C | $9.4 \times 10^{-6}$ | 5.92 | 35 |

(1)0.2% Pd/Charcoal Matheson, Coleman & Bell
(3)10% PdAl$_2$O$_3$ Engelhard Industries, Inc.
(4)5% Pd/CaCo$_3$ Engelhard Industries, Inc.
(5)5% Pd/CaCo$_3$ Engelhard Industries, Inc.
(6)1% Pt/Charcoal Matheson, Coleman & Bell
(7)5% Rh/Al$_2$O$_3$ Engelhard
(8)5% Ru/C Engelhard
(9)Union Carbide porous carbon carrier (A > 1000 m$^2$/gm) first impregnated with metal nitrate solution, dried and then reduced with hydrogen at 500° C.

The above results demonstrate the superiority of supported palladium, platinum and rhodium when compared to other supported catalysts.

Illustrative Embodiment III

To an 80 ml glass-lined autoclave were charged $2.7 \times 10^{-5}$ moles of palladium of the appropriate palladium compound listed in Table III, $5.4 \times 10^{-5}$ moles of (isopropyl)$_3$ phosphine, 2.5 g of triethylamine-formic acid salt, 10 ml of pyridine and 2 g of 1,3-butadiene. The stirred reactor was heated to 45° C. for 1 hour, cooled and the product was analyzed by gas chromatography for the amount of 1,7-octadiene present. The above reaction was repeated adding using 0.01 g ($9.4 \times 10^{-6}$ moles) of 10% Pd/C (Baker<100 mesh). In all cases, the concentration of soluble palladium catalyst was $1.8 \times 10^{-3}$ molar. The results are shown in Table III.

TABLE III

| Pd Salt Utilized | Co—Catalyst | Rate, % 1,7-Octadiene In Product Per Hour | % of Butadiene Reactant Converted to 1,7-Octadiene In 1 Hour |
|---|---|---|---|
| Pd (NO$_3$)$_2$(OH)$_2$ (10% aqueous solution) | None | 5.87 | 34.5 |
| Pd (NO$_3$)$_2$(OH)$_2$ | None | 5.61 | 33.0 |
| Pd (acetate)$_2$ | None | 0.81 | 4.8 |
| Pd (acetylacetonate)$_2$ | None | 1.86 | 10.9 |
| Pd SO$_4$ | None | 0.65 | 3.8 |
| Pd Cl$_2$ | None | 0.48 | 2.8 |
| Pd (NO$_3$)$_2$(OH)$_2$ (10% aqueous solution) | 10% Pd/C | 16.0 | 94 |
| Pd (NO$_3$)$_2$(OH)$_2$ | 10% Pd/C | 14.67 | 86.5 |
| Pd (acetate)$_2$ | 10% Pd/C | 4.51 | 26.5 |
| Pd (acetylacetonate)$_2$ | 10% Pd/C | 4.10 | 24.1 |
| Pd SO$_4$ | 10% Pd/C | 5.11 | 30.0 |
| Pd Cl$_2$ | 10% Pd/C | 1.48 | 8.7 |

The above results show that the rate enhancement effect is shown for a number of different solubilized palladium salts.

Illustrative Embodiment IV

To an 80 ml glass-lined autoclave were charged $0.9 \times 10^{-5}$ moles as a 10% water solution of Pd(NO$_3$)$_2$(OH)$_2$, $1.8 \times 10^{-5}$ moles (isopropyl)$_3$ phosphine, 2.5 grams of triethylamine formic acid salt, 10 milliliters of pyridine and 2 grams of 1,3-butadiene. The stirred reactor was heated to 45° C. for 1 hour, cooled and the process was analyzed by gas chromatography for the amount of 1,7-octadiene present. This case provided the base case for solubilized palladium alone and provides one-third the amount of solubilized palladium as does Illustrative Embodiment I (the concentration of soluble palladium being $0.6 \times 10^{-3}$ molar in this case versus $1.8 \times 10^{-3}$ molar in Illustrative Embodiment I). The results are shown in Table IV.

The above experiment was repeated for additional times using 0.001 g, 0.001 g, 0.01 g and 0.1 g of 10% w palladium on carbon catalyst (Baker and Co., Inc.) in addition to the base case concentration of solubilized catalyst. The results are shown in Table IV. Column 3 gives the average rate (R) of formation of 1,7-octadiene in the product per hour. Column 4 reports the percentage of the butadiene reactant originally present in the reaction which is converted to the desired 1,7-octadiene product in one hour reaction time. Column 5 is the rate (R) normalized to the rate obtained using solubilized palladium alone ($R_o$), and column 6 gives the ratio of supported palladium to solubilized palladium.

TABLE IV

| Moles of Palladium Added | | Rate % w 1,7-Octadiene In Product Per Hour | % of Butadiene Reactant Converted 1,7-Octadiene In 1 Hour | Normalized Rate $R/R_o$ | Supported Pd/ Solubilized Pd |
| --- | --- | --- | --- | --- | --- |
| Solubilized | Supported | | | | |
| $9 \times 10^{-6}$ | — | 1.70 | 10 | 1.0 | — |
| $9 \times 10^{-6}$ | $9.4 \times 10^{-5}$ | 0.70 | 4.1 | 0.4 | 10 |
| $9 \times 10^{-6}$ | $9.4 \times 10^{-6}$ | 1.80 | 10.6 | 1.06 | 1 |
| $9 \times 10^{-6}$ | $9.4 \times 10^{-7}$ | 3.3 | 19.4 | 1.94 | 0.1 |
| $9 \times 10^{-6}$ | $9.4 \times 10^{-8}$ | 2.7 | 15.9 | 1.59 | 0.01 |

Illustrative Embodiment V

To an 80 ml glass-lined autoclave were charged $2.7 \times 10^{-5}$ moles of palladium acetate, $1.08 \times 10^{-4}$ moles of (isopropyl) phosphine, 2.5 g of triethylamine-formic acid salt, 10 ml of pyridine and 5 g of a BBB stream containing 40.34% 1,3-butadiene. The stirred reactor was heated to 40° C. for 1 hour, cooled and the product was analyzed by gas chromatography for the amount of 1,7-octadiene present, giving a rate of 0.12% w 1,7-octadiene per hour. The above reaction was repeated adding 0.01 g of 10% Pd/C (Baker 100 mesh) and 2% hydrogen basis butadiene to the reaction mixture. The rate was increased to 3.98% w 1,7-octadiene per hour.

What is claimed is:

1. In the process for preparing 1,7-octadiene by hydrodimerizing 1,3-butadiene in the presence of a solubilized palladium catalyst, a tertiary phosphine, formic acid, a base and optionally an organic solvent wherein the temperature ranges from about 0° C. to about 100° C., the solubilized palladium ranges from about $10^{-1}$ to about $10^{-6}$ molar, the mole ratio of tertiary phosphine to solubilized palladium is at least 1 and the molar ratio of base to formic acid is at least 1, the improvement which comprises utilizing as a co-catalyst a metal catalyst supported on an inert carrier wherein said metal is selected from the group consisting of palladium, platinum, rhodium, and mixtures thereof and is present on the carrier in amounts ranging from about 0.0001 to about 30 percent by weight of total supported catalyst, and the ratio of the metal in the supported catalyst to the solubilized palladium ranges from about 0.0035 to about 0.35.

2. The process of claim 1 wherein the support is siliceous, aluminous or carbonaceous in nature.

3. The process of claim 1 wherein the metal supported on the carrier ranges from about 0.001 to about 10 percent by weight of total supported catalyst.

4. The process of claim 1 wherein the metal supported on the carrier ranges from about 0.001 to about 3 percent by weight of total supported catalyst and the solubilized palladium ranges from about $10^{-2}$ to about $10^{-3}$ molar.

5. The process of claim 4 wherein the solubilized palladium is palladium nitrate.

6. The process of claim 1 where the 1,3-butadiene is contained in a BBB stream from an oil pyrolysis unit and from about 0.2 to about 4 percent by weight of hydrogen is added to the reaction mixture.

* * * * *